United States Patent [19]

Schaper et al.

[11] 4,267,075

[45] * May 12, 1981

[54] PERFUME COMPOSITIONS CONTAINING ESTERS OF 3,5,5-TRIMETHYLHEXANOIC ACID

[75] Inventors: Ulf-Armin Schaper, Düsseldorf; Jens Conrad, Hilden; Klaus Bruns, Krefeld-Traar, all of Fed. Rep. of Germany

[73] Assignee: Henkel Kommanditgesellschaft auf Aktien, Dusseldorf-Holthausen, Fed. Rep. of Germany

[ * ] Notice: The portion of the term of this patent subsequent to Dec. 21, 1995, has been disclaimed.

[21] Appl. No.: 969,205

[22] Filed: Dec. 13, 1978

[30] Foreign Application Priority Data

Dec. 23, 1977 [DE] Fed. Rep. of Germany ....... 2757559

[51] Int. Cl.[3] .......................... C11B 9/00; A61K 7/46

[52] U.S. Cl. ................................ 252/522 R; 424/358; 252/89.1; 252/108; 252/174; 252/369; 26/1; 424/76

[58] Field of Search ........................................ 252/522

[56] References Cited

U.S. PATENT DOCUMENTS 4,126,585 11/1978 Conrad et al. ....................... 252/522

OTHER PUBLICATIONS

E. E. Turner et al., J. Chem. Soc., pp. 2543–2545, 1951.

J. Prakt. Chem. (4), 14, 71, 1961.

*Primary Examiner*—Veronica O'Keefe

*Attorney, Agent, or Firm*—Hammond & Littell, Weissenberger and Muserlian

[57] ABSTRACT

A perfumery composition consisting essentially of from 1% to 50% by weight of an ester of 3,5,5-trimethylhexanoic acid of the formula

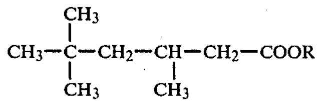

wherein R is a member selected from the group consisting of alkyl having from 1 to 5 carbon atoms, alkenyl having from 3 to 5 carbon atoms and alkynyl having from 3 to 5 carbon atoms, and the remainder customary constituents of perfumery compositions; as well as the method of perfuming employing the perfumery composition.

5 Claims, No Drawings

PERFUME COMPOSITIONS CONTAINING ESTERS OF 3,5,5-TRIMETHYLHEXANOIC ACID

This invention relates to perfume ingredients consisting of 3,5,5-trimethyl-hexanoic acid esters and to perfume compositions containing these ingredients.

OBJECTS OF THE INVENTION

An object of the present invention is the development of perfumery compositions based on esters of 3,5,5-trimethylhexanoic acid.

Another object of the present invention is the development of a perfumery composition consisting essentially of from 1% to 50% by weight of an ester of 3,5,5-trimethylhexanoic acid of the formula

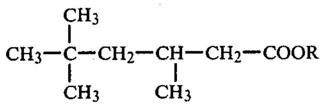

wherein R is a member selected from the group consisting of alkyl having from 1 to 5 carbon atoms, alkenyl having from 3 to 5 carbon atoms and alkynyl having from 3 to 5 carbon atoms, and the remainder customary constituents of perfumery compositions.

A further object of the invention is the development of an improvement in the process of imparting a pleasing odor to an object comprising applying a perfume composition thereto, the said improvement consisting of employing the above perfumery composition as said perfume composition.

These and other objects of the present invention will become more apparent as the description thereof proceeds.

DESCRIPTION OF THE INVENTION

It has now been found that 3,5,5-trimethylhexanoic acid esters corresponding to the following general formula:

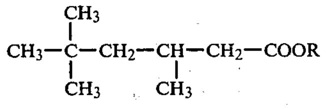

in which R represents a saturated, unsaturated, straight or branched chain aliphatic hydrocarbon group having from 1 to 5 carbon atoms, may advantageously be used as perfume ingredients which have a wide variety of odoriferous characteristics.

More particularly, therefore, the present invention relates to a perfumery composition consisting essentially of from 1% to 50% by weight of an ester of 3,5,5-trimethylhexanoic acid of the formula

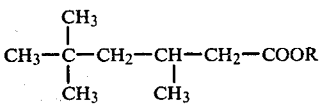

wherein R is a member selected from the group consisting of alkyl having from 1 to 5 carbon atoms, alkenyl having from 3 to 5 carbon atoms and alkynyl having from 3 to 5 carbon atoms, and the remainder customary constituents of perfumery compositions.

The preparation of the 3,5,5-trimethylhexanoic acid esters to be used as perfume ingredients according to the invention is carried out according to the usual methods of organic chemistry, by the reaction of 3,5,5-trimethylhexanoic acid or the corresponding acid chloride with the desired alcohol. 3,5,5-trimethylhexanoic acid itself is obtained as the main reaction product of the hydroformylation of di-isobutylene, followed by oxidation of the intermediate products. The resulting mixture of acids is sold under the name of "Isononanoic acid" and generally contains about 90% of 3,5,5-trimethylhexanoic acid. Ordinary commercial isononanoic acid may be used as starting material for the preparation of the 3,5,5-trimethylhexanoic acid esters which are to be used as perfume ingredients, because the small quantities of by-products present in many cases have no deleterious effects.

Suitable 3,5,5-trimethylhexanoic acid esters for use according to the invention include, for example, alkyl esters having from 1 to 5 carbon atoms in the alkyl such as the methyl, ethyl, propyl, isopropyl, butyl, isobutyl, tertiary butyl and pentyl esters, alkenyl esters having from 3 to 5 carbon atoms in the alkenyl such as the allyl ester, and alkynyl esters having from 3 to 5 carbon atoms in the alkynyl such as the propargyl ester, of 3,5,5-trimethylhexanoic acid. The most important among these, because of their interesting odoriferous characteristics, are the methyl ester and the ethyl ester.

The 3,5,5-trimethylhexanoic acid esters to be used according to the invention are valuable perfume ingredients which have characteristic scents ranging from the floral to the fruity and woody. A particular advantage of the perfume ingredients according to the invention is the ease with which they can be combined to produce novel and interesting nuances of scent.

The 3,5,5-trimethylhexanoic acid esters to be used as perfume ingredients according to the invention may be mixed with other perfume ingredients in various proportions to produce new perfumery compositions. The proportion of 3,5,5-trimethylhexanoic acid esters in the perfumery compositions is generally within the range of from 1% to 50% by weight, based on the whole composition. The remainder of the perfumery composition is conventional perfume constituents. One or more additional perfumes can be used in combination with the 3,5,5-trimethylhexanoic acid esters of the invention.

Such compositions may be used as perfumes alone or for scenting cosmetics such as creams, lotions, toilet water, aerosols and toilet soaps and commercial products such as detergents, cleaning agents, disinfectants and textile finishes.

The invention thus also includes a process of imparting a pleasant odor to a product comprising adding thereto from 0.05% to 2% by weight, based on the total product, of a perfumery composition containing the 3,5,5-trimethylhexanoic acid esters of the invention, as a scenting agent.

The "Isononyl alcohol," used as a starting material in the production of "Isononanoic acid" by oxidation, is obtained by reduction of the product of hydroformylation of diisobutylene. This commercial alcohol contains 3,5,5-trimethylhexanol as its main component. Both isononyl alcohol and its acetate are used as perfume components in the perfume industry. The odor of these compounds is very different from that of the 3,5,5-trimethylhexanoic acid esters used according to the invention. Although both the methyl ester and the ethyl ester of 3,5,5-trimethylhexanoic acid have long been known in the literature (J. Chem. Soc. 1951, 2545 and J. Prakt. Chem. (4), 14, 71 (1961), the possibility of using them as perfume ingredients has not previously been described. It was therefore not possible to draw any conclusion about the odoriferous properties of the esters of 3,5,5-trimethylhexanoic acid from the suitability of the esters of isononyl alcohol as perfume components.

The invention will now be described more fully with reference to the following examples, which are not to be deemed limitative of the invention in any respect.

EXAMPLES

The following esters to be used accoring to the invention were prepared by the usual method of esterification of 3,5,5-trimethylhexanoic acid with the corresponding alcohol:

(A) Methyl 3,5,5-trimethylhexanoate
$BP_{12}$ 70° C. $n_D^{20}$ 1.4200
Odor: note of Bergamot (B) Ethyl 3,5,5-trimethylhexanoate
$BP_{12}$ 79° C. $n_D^{20}$ 1.4205
Odor: note of apple and wine yeast (C) Propyl 3,5,5-trimethylhexanoate
$BP_{15}$ 101° C. $n_D^{20}$ 1.4231
Odor: fruity, note of wine yeast (D) Isopropyl 3,5,5-trimethylhexanoate
$BP_{16}$ 91° C. $n_D^{20}$ 1.4193
Odor: woody, fruity (E) n-Butyl 3,5,5-trimethylhexanoate
$BP_{16}$ 117° C. $n_D^{20}$ 1.4268
Odor: fatty, note of walnut and lovage (F) Allyl 3,5,5-trimethylhexanoate
$BP_{15}$ 101° C. $n_D^{20}$ 1.4328
Odor: flowery, green, fruity-acid (G) Propargyl 3,5,5-trimethylhexanoate
$BP_{15}$ 112° C. $n_D^{20}$ 1.4387
Odor: note of geranium, pelargonium and carveyl acetate

EXAMPLE 1

Eau de Cologne formulation

| | Parts by Weight |
|---|---|
| Methyl 3,5,5-trimethylhexanoate | 150 |
| Oil of Bergamot | 260 |
| Lemon grass oil | 250 |
| Petit-grain oil bigarade | 100 |
| Portugal oil Guinea | 80 |
| Neroli oil bigarade | 50 |
| French lavender oil | 35 |
| Tunisian oil of Rosemary | 30 |
| Linaloe oil | 20 |
| Isonal, Givauden | 20 |

-continued

| | Parts by Weight |
|---|---|
| Sauge Sclaree | 5 |
| | 1,000 |

EXAMPLE 2

Fruit/green complex Perfume

| | |
|---|---|
| Ethyl 3,5,5-trimethylhexanoate | 100 |
| Phenylethyl alcohol | 250 |
| Portugal oil, sweet, Guinea | 180 |
| Oil of Bergamot | 170 |
| Geranyl acetate | 100 |
| Diphenyl methane | 70 |
| Hexyl acetate | 50 |
| Aldehyde C16 (so called) | 40 |
| Undecalactone | 30 |
| Styrallyl acetate | 10 |
| | 1,000 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A perfumery composition comprising from 1% to 50% by weight of an ester of 3,5,5-trimethylhexanoic acid of the formula

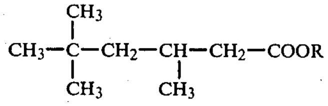

wherein R is a member selected from the group consisting of alkyl having from 1 to 5 carbon atoms, alkenyl having from 3 to 5 carbon atoms and alkynyl having from 3 to 5 carbon atoms, and the remainder customary constituents of perfumery compositions.

2. The perfumery composition of claim 1 wherein R is methyl.

3. The perfumery composition of claim 1 wherein R is ethyl.

4. The perfumery composition of claim 1 which contains at least one further additional perfume.

5. A method of imparting a pleasant odor to a product comprising applying thereto from 0.05% to 2% by weight, relative to the total product, of the perfumery composition of claim 1, comprising from 1% to 50% by weight of said ester of 3,5,5-trimethylhexanoic acid and the remainder customary constituents of perfumery compositions as a scenting agent.

* * * * *